US010702341B2

(12) United States Patent
Shochat

(10) Patent No.: US 10,702,341 B2
(45) Date of Patent: Jul. 7, 2020

(54) DYNAMIC PLANNING METHOD FOR NEEDLE INSERTION

(71) Applicant: XACT ROBOTICS LTD., Caesarea (IL)

(72) Inventor: Moran Shochat, Zichron Yaakov (IL)

(73) Assignee: XACT ROBOTICS LTD, Caesaria (IL)

( * ) Notice: Subject to any disclaimer, the term of this patent is extended or adjusted under 35 U.S.C. 154(b) by 0 days.

(21) Appl. No.: 16/282,369

(22) Filed: Feb. 22, 2019

(65) Prior Publication Data

US 2019/0254749 A1 Aug. 22, 2019

Related U.S. Application Data

(63) Continuation of application No. 15/122,421, filed as application No. PCT/IL2015/050230 on Mar. 4, 2015, now Pat. No. 10,245,110.

(Continued)

(51) Int. Cl.
*A61B 34/10* (2016.01)
*A61B 6/00* (2006.01)
(Continued)

(52) U.S. Cl.
CPC ............ *A61B 34/10* (2016.02); *A61B 6/5235* (2013.01); *A61B 8/5246* (2013.01);
(Continued)

(58) Field of Classification Search
CPC ....... A61B 6/12; A61B 17/3403; A61B 34/10; A61B 6/5235; A61B 8/0841;
(Continued)

(56) References Cited

U.S. PATENT DOCUMENTS 6,400,979 B1 6/2002 Stoianovici et al.
6,580,938 B1 * 6/2003 Acker .................... A61B 5/415
600/424
(Continued)

FOREIGN PATENT DOCUMENTS

CN 101869501 A 10/2010
CN 102949240 A 3/2013
(Continued)

OTHER PUBLICATIONS

International Search Report and Written Opinion of the ISA, in PCT/IL2015/050230, dated Jun. 29, 2015.
(Continued)

*Primary Examiner* — Jingge Wu
(74) *Attorney, Agent, or Firm* — Daniel Feigelson; Fourth Dimension IP

(57) ABSTRACT

A method of planning an image-guided interventional procedure to be performed on a patient, where expected motion of the patient, such as that of a breathing cycle, is determined on a sequence of preoperative images, and the procedure trajectory is planned accordingly. The method takes into account the initial positions of the interventional entry, the target region, and any obstructions or forbidden regions between the entry point and the target region, and uses object tracking methods of image processing on the preoperative images to determine how the positions of these three elements change relative to each other during the patient's motion cycle. The method may automatically search in at least some of the preoperative images taken at different temporal points of the motion cycle, for a path connecting the entry point with the target and avoiding the obstacles, which provides minimal lateral pressure on the patient's tissues.

12 Claims, 11 Drawing Sheets

Related U.S. Application Data

(60) Provisional application No. 61/966,754, filed on Mar. 4, 2014.

(51) Int. Cl.
| | | |
|---|---|---|
| *A61B 8/08* | (2006.01) | |
| *G06T 7/11* | (2017.01) | |
| *G06T 7/00* | (2017.01) | |
| *A61B 6/12* | (2006.01) | |
| *A61B 17/00* | (2006.01) | |
| *A61B 17/34* | (2006.01) | |

(52) U.S. Cl.
CPC .............. *G06T 7/0012* (2013.01); *G06T 7/11* (2017.01); *A61B 6/12* (2013.01); *A61B 6/5217* (2013.01); *A61B 8/0841* (2013.01); *A61B 8/5223* (2013.01); *A61B 17/3403* (2013.01); *A61B 2017/00699* (2013.01); *A61B 2017/3413* (2013.01); *A61B 2034/105* (2016.02); *A61B 2034/107* (2016.02); *G06T 2207/10081* (2013.01)

(58) Field of Classification Search
CPC ... A61B 8/5223; A61B 8/5246; G06T 7/0012; G06T 7/0081; G06T 2210/41
See application file for complete search history.

(56) References Cited

U.S. PATENT DOCUMENTS

| | | | |
|---|---|---|---|
| 7,008,373 B2 | 3/2006 | Stoianovici et al. | |
| 7,167,180 B1 | 1/2007 | Shibolet et al. | |
| 7,833,221 B2 | 11/2010 | Voegele et al. | |
| 8,348,861 B2 | 1/2013 | Glozman et al. | |
| 8,663,130 B2 | 3/2014 | Neubach et al. | |
| 10,485,577 B2* | 11/2019 | LaConte | A61F 9/007 |
| 2005/0033160 A1 | 2/2005 | Yamagata et al. | |
| 2005/0267359 A1 | 12/2005 | Hussaini et al. | |
| 2006/0089625 A1 | 4/2006 | Voegele et al. | |
| 2008/0234700 A1 | 9/2008 | Trovato | |
| 2009/0281452 A1 | 11/2009 | Pfister et al. | |
| 2010/0082040 A1 | 4/2010 | Sahni | |
| 2010/0130853 A1 | 5/2010 | Chandonnet et al. | |
| 2011/0125011 A1 | 5/2011 | Wieczorek et al. | |
| 2012/0046545 A1 | 2/2012 | Averbuch et al. | |
| 2012/0215096 A1 | 8/2012 | Gilboa et al. | |
| 2012/0226145 A1 | 9/2012 | Chang et al. | |
| 2012/0265098 A1* | 10/2012 | McGhie | A61B 17/3403 |
| | | | 600/567 |
| 2012/0302873 A1 | 11/2012 | Tajima et al. | |
| 2013/0225984 A1 | 8/2013 | Cheng | |
| 2013/0229504 A1 | 9/2013 | Cheng | |
| 2014/0086470 A1 | 3/2014 | Mukumoto | |
| 2018/0360609 A1* | 12/2018 | Steines | A61F 2/30 |

FOREIGN PATENT DOCUMENTS

| | | |
|---|---|---|
| KR | 20130116970 A | 10/2013 |
| WO | 2006/081409 A2 | 8/2006 |
| WO | 2013114994 A1 | 8/2013 |
| WO | 2015132787 A1 | 9/2015 |

OTHER PUBLICATIONS

English translation of OA issued in JP 2016-555680 dated Sep. 25, 2018.
English translation of OA issued in CN 201580011357.2 dated Oct. 9, 2018.
Opinion from European Patent Office regarding EP-A-157589045.
CN 102949240 Machine Translation (by EPO and Google); published on Mar. 6, 2013, Gao Xin et al.
KR 20130116970 Machine Translation (by EPO and Google); published on Oct. 25, 2013, Biospace Co. Ltd.
CN 101869501 Machine Translation (by EPO and Google); published on Oct. 27, 2010, Beijing University of Chinese Medicine.

* cited by examiner

DYNAMIC PLANNING METHOD FOR NEEDLE INSERTION

RELATED APPLICATIONS

This application is a continuation of U.S. Ser. No. 15/122,421, entitled "DYNAMIC PLANNING METHOD FOR NEEDLE INSERTION" and filed on Aug. 30, 2016 as the national stage of PCT/IL2015/050230, having the same title and filed Mar. 4, 2015, which claims the benefit of provisional application No. 61/966,754, filed Mar. 4, 2014.

FIELD OF THE INVENTION

The present invention relates to systems and methods of planning automated (e.g., robotically controlled) needle insertion procedures, especially taking into account the motion of the insertion point, the target point and any region between them which should be avoided, as a result of cyclic body motion, such as the breathing cycle.

BACKGROUND

Current static needle insertion planning uses a preoperative image of the region of interest including the point of entry, the target and any obstacles en route which have to be avoided. An obstacle can be understood to mean a real physical obstacle, such as a rib, or it can mean a sensitive area where damage could be caused by entry of the needle, such as a major blood vessel or an important nerve. The problem is that this procedure does not take into account cyclical motion of the patient, such as from breathing, which could cause the entry point, the target point and the position of any obstacles en route to move in some sort of reproducible cycle from their initial positions relative to each other.

In existing methods, the progress of the needle (or of the process) is reviewed intraoperatively and the images are synchronized to the motion cycle, and then appropriate correction is taken during the motion cycle. This is the method used in following heart motion and pulsating arteries during angioplasty, or during valve correction operations, with the heart beat continuing during the procedure. Such methods have a serious disadvantage in that they require constant, generally fluoroscopic, imaging during the complete duration of the procedure, with concomitant significant radiation exposure for the patient and the medical staff. In other known methods, such as that shown in U.S. Pat. No. 7,833,221 to J. W. Voegele et al, for "System and Method for Treatment of Tissue using the Tissue as a Fiducial", there is described an ultrasound method in which the respiration cycle is monitored to indicate when a tissue target is approaching the dwell position—the brief pause between inhalation and exhalation in each respiratory cycle—so that the surgeon can insert his surgical device to a tumor when the tumor is positioned according to an image of the tumor generated at the dwell position. However, such methods limit insertion of a tool to a single target point imaged non-iteratively at a repeated fixed point in the breathing cycle. Further, in some existing methods, as disclosed, for example, in U.S. Pat. No. 7,008,373 to Stoianovici et al, for "System and method for robot targeting under fluoroscopy based on image servoing", it is preferred that patient respiration is shortly stopped during the image acquisition prior to target selection and during needle insertion, thus requiring the physician to rely solely on the patient's ability to hold his breath at the required times and for the required durations.

SUMMARY

The current application attempts to provide a method whereby the expected motion of the patient is determined at the planning stage on the preoperative images, and the trajectory is planned accordingly, taking into account not only the initial positions of the entry, obstruction and target points, but also how these three elements are expected to move relative to each other during the course of the patient's motion cycle.

According to some implementations, a sequence of video frames is taken of the region of interest, which follows the complete cycle of the motion, such as a breathing cycle. Alternatively, a series of cycles can be recorded, which can then be averaged. The video frames are generally taken from the CT scans of the patient's region of interest. In some implementations, the user/doctor/physician (the terms "user", "doctor" and "physician" are used interchangeably throughout this disclosure) marks the target point, the obstacles en route and an initial point of entry, on an initial static image taken from the video sequence of the region of interest. The doctor's experience of the best trajectory to follow preferably plays a role in choosing the entry point. In some implementations, the user does not define the initial trajectory, since the system software is adapted to automatically search for a path connecting the point of entry with the target and avoiding the obstacles en route, which provides minimal lateral pressure on the patient's tissues. In so doing, the system can also select the appropriate entry angle at the input point chosen. In other implementations, the system may require or allow for the doctor to select the entry angle of the needle.

From the video sequence, there can be determined how the positions of the point of entry, the obstacles, and the target point change from frame to frame during the course of the patient's motion cycle.

In some implementations, an initial preplanned trajectory, which is calculated taking into account the position of the entry point, target point and obstacle/s en route in an initial static image, is followed through the series of frames comprising a complete body motion cycle. If, during the whole of the cycle, a safe trajectory is indicated, taking into account all of the motions and a safety margin around obstructions, then the doctor can use his initial preplanned static trajectory for the entire breathing cycle. If there is a problem with the preplanned trajectory in one or more of the subsequent frames, then, where possible, the doctor can modify his selection of the element locations in these frames (e.g., reduce the safety margin around an obstacle) and/or in the initial static image (e.g., choose a different entry point and/or change the entry angle) to resolve the problem and then repeat the path verification in the entire video sequence. Alternatively, the doctor/user may select a different image (also sometimes referred to in this disclosure as "image frame", or simply as "frame"), representing a different time point in the body motion cycle, to use as the initial static image for the calculation of the trajectory. In this method implementation, a single trajectory, calculated based on the locations of the target and obstacle in one initial image frame, is checked on all remaining image frames. Since the locations of the target and obstacle might be different in a different image frame, a different trajectory is likely to be calculated. This new trajectory, unlike its predecessor, may be acceptable for all the image frames. This process can be repeated iteratively until a safe trajectory is indicated throughout the whole of the cycle.

In some implementations, during the planning stage, after the doctor has selected the entry point and has marked the target and en-route obstacles in the first CT image, the system algorithm runs through the series of frames comprising a complete body motion cycle, and, taking into account how the entry point, target and obstacles move at each frame, calculates a single trajectory using the initial entry point, that will reach the target yet avoid all obstacles at every one of the frames in the complete cycle.

In other implementations, the system algorithm may run through the series of frames and calculate for each of the frames, separately, an optimal trajectory that will reach the target yet avoid all obstacles at that particular frame. In such implementations, all or at least one of the calculated trajectories may be followed through all of the other frames in the sequence, and one of the trajectories which is found to be applicable to the entire series of frames may be selected for the needle insertion procedure. Such a trajectory may be the trajectory having the minimal curvature and/or the shortest distance from the entry point to the target point, for example. In some implementations, an average of all or at least two of the trajectories may be calculated and selected.

According to some implementations, the system can check the calculated trajectory/trajectories and if it appears from an inspection of the frames in the cycle that for a particular trajectory, the needle at any part of the cycle diverts more than a predetermined amount from an optimum trajectory, meaning that excessive lateral pressure would be exerted on the tissues of the patient, then that entry point can be abandoned and the doctor/user can repeat the planning procedure with a different entry point, with the aim of providing a better trajectory, i.e. one with less severe curvature and hence generating less lateral pressure on the tissues of the patient. Alternatively, the same entry point can be maintained, but the initial orientation of the needle at the entry point can be changed in order to select an alternative initial planned trajectory which may result in a better overall trajectory for the entire procedure. In some implementations, both a new entry point and a new entry angle may be selected. The dynamically chosen trajectories can be optionally shown to the user (e.g., attending physician), for confirmation that they are surgically and safety-wise acceptable.

The above described planning methods may be subsequently utilized when the doctor is performing the needle insertion procedure by selecting one or more time frames during the cycle of motion of the patient, in which the trajectory shows the minimum curvature, for example, and limiting the needle insertion steps to be performed only during that time frame or those time frames of the complete motion cycle. For example, for the case of a breathing cycle, insertion could be limited to that or those time frames when the patient has fully expired his breath. This procedure thus enables the insertion to be performed without the need to amend the angle of entry of the needle, thereby enabling the entire insertion procedure to be performed, in contrast to prior art procedures, without any intra-procedural imaging intervention at all for the purposes of following the patient's body motion, or for safety reasons, with minimal selected imaging. Therefore, one substantial advantage over prior art methods, engendered by use of the planning methods described in this application is that it enables the procedure to be performed with reduced radiation exposure to the patient and medical staff. Obviously, any fluoroscopic imaging required for the implementation of the needle guidance procedure itself, as opposed to for following body motion, cannot be avoided.

Although some method implementations have been described relating to inspection of or taking into account every one of the frames of the sequence, it is to be understood that the method can also be executed using only some of the frames of the sequence, so long as the number selected are sufficiently close together that extreme situations are not generated in the intervening missed frames.

In addition, although the method has been described in this disclosure using two-dimensional images, it is to be understood that it is equally applicable using three-dimensional images, which may be the preferred situation when CT scans are being used as the preoperative images on which the dynamic path is to be calculated. Furthermore, the described method implementations are not limited to the use of CT scans, and they can be implemented using images generated by other imaging systems, such as an X-ray fluoroscopic system, an ultrasonic system, or an MRI system.

One exemplary implementation involves a method of planning an image-guided interventional procedure in a region of interest of a subject, comprising:

(a) obtaining a plurality of time-separated images of the region of interest, (b) defining on a first image of the plurality of images, an entry point, a target point and one or more regions into which entry by the interventional procedure is forbidden, (c) calculating a trajectory for the interventional procedure between the entry point and the target point, which avoids entry into any of the one or more forbidden regions, (d) selecting a second image of the plurality of images generated at a time different from that at which the first of the plurality of images was generated, (e) determining changes in the position of the entry point, target point and any regions into which entry by the interventional procedure is forbidden in the second image of the plurality of images, and (f) repeating step (c) on the second image of the plurality of images based on the changes in position determined in step (e).

Such a method may further comprise the step of selecting on the first image of the plurality of images, an entry angle for the interventional procedure at the entry point. Additionally, these methods may further comprise the step of determining if one or more characteristics of at least one of the calculated trajectories exceeds a predetermined level along any part of the at least one of the calculated trajectories' length. The one or more characteristics may optionally be the curvature of the trajectory, or the distance from any of the one or more regions into which entry by the interventional procedure is forbidden. If it evolves that one or more characteristics of at least one of the calculated trajectories exceeds a predetermined level along a part of the at least one of the calculated trajectories' length, the method may include repeating the planning using an alternative entry point.

In any of the above described methods involving the selection of an entry angle, if one or more characteristics of at least one of the calculated trajectories exceeds a predetermined level along a part of at least one of the calculated trajectories' length, then the planning may be repeated using at least one of an alternative entry point and an alternative entry angle. In the case of the curvature characteristic, the method may further comprise the step of selecting that planning which generates a trajectory having a lesser curvature along any part of its length than any trajectory provided by a different planning.

Additionally, alternative implementations of any of the above-described systems may further comprise the step of storing one or more of the calculated trajectories.

Still other exemplary implementations involve the above described methods and further comprising the steps of:

(a) determining if one or more of the calculated trajectories are applicable to each of the plurality of images, and (b) if one or more of the calculated trajectories is determined to be applicable to each of the plurality of images, determining which trajectory of the one or more applicable trajectories is optimal for all of the plurality of images.

In the last described method, the step of determining if one or more of the calculated trajectories is applicable to each of the plurality of images may comprise determining if one or more of the calculated trajectories terminates at the target point in each of the plurality of images and avoids entry into any of the one or more forbidden regions in each of the plurality of images. Furthermore, the step of determining which trajectory of the one or more applicable trajectories is optimal for all of the plurality of images may comprise one or more of:

(a) determining which of the one or more applicable trajectories comprises a lesser curvature, and (b) determining which of the one or more applicable trajectories comprises a lesser distance between the entry point and the target point.

These methods may further comprise the step of selecting that planning which generates a trajectory having a lesser curvature along any part of its length than any trajectory provided by a different planning.

Yet other implementations perform a method of planning an image-guided interventional procedure in a region of interest of a subject, comprising:

(a) obtaining a plurality of time-separated images of the region of interest, (b) defining on a first image of the plurality of images, an entry point, a target point and one or more regions into which entry by the interventional procedure is forbidden, (c) calculating a trajectory for the interventional procedure between the entry point and the target point, which avoids entry into any of the forbidden regions, (d) selecting a second image of the plurality of images generated at a time different from that at which the first image of the plurality of images was generated, (e) determining changes in the position of the entry point, target point and any regions into which entry by the interventional procedure is forbidden in the second image of the plurality of images, and (f) determining if in the second image of the plurality of images the calculated trajectory connects between said entry point and said target point and avoids entry into any of said forbidden regions.

This method may also include a step of determining if one or more characteristics of the calculated trajectory exceeds a predetermined level along any part of the calculated trajectory length. The one or more characteristics may be curvature.

An alternative implementation performs a method of planning an image-guided interventional procedure in a region of interest of a subject, comprising:

(a) obtaining a plurality of time-separated images of the region of interest, (b) defining on a first image of the plurality of images, an entry point, a target point and one or more regions into which entry by the interventional procedure is forbidden, (c) selecting a second image of the plurality of images generated at a time different from that at which the first image of the plurality of images was generated, (d) determining changes in the position of the entry point, target point and any regions into which entry by the interventional procedure is forbidden in the second image of the plurality of images, and (e) calculating a trajectory for the interventional procedure between the entry point and the target point, which avoids entry into any of the one or more forbidden regions in the first image of the plurality of images and in the second image of the plurality of images.

This method may further comprise the step of determining if one or more characteristics of at least one of the calculated trajectories exceeds a predetermined level along any part of the at least one of the calculated trajectories' length. That one or more characteristics may be curvature.

Additionally, alternative implementations may further involve a method of planning an image-guided interventional procedure in a region of interest of a subject, comprising:

(a) calculating a trajectory for the interventional procedure between an entry point and a target point, which avoids entry into any of one or more forbidden regions, wherein the entry point, the target point and the one or more forbidden regions have been defined on a first image of a plurality of time-separated images of the region of interest, (b) determining changes in the position of the entry point, target point and any regions into which entry by the interventional procedure is forbidden in a second image of the plurality of images generated at a time different from that at which the first image of the plurality of images was generated, and (c) repeating step (a) on the a second image of the plurality of images based on the changes in position determined in step (b).

Such a method can further include the step of obtaining the plurality of time-separated images. Additionally, the method may further comprise the step of storing the entry point, the target point and the one or more regions into which entry by the interventional procedure is forbidden.

According to yet further implementations of the methods described in the present application, there is provided a method of planning an image-guided interventional procedure in a region of interest of a subject, comprising:

(a) imaging the region of interest, the imaging comprising generating a plurality of time-separated images, (b) defining on a first image of the plurality of images, an entry point, a target point and one or more regions into which entry by the interventional procedure is forbidden, (c) calculating a trajectory for the interventional procedure between the entry point and the target point, which avoids entry into any of the one or more forbidden regions, (d) selecting a second image of the plurality of images generated at a time different from that at which the first image of the plurality of images was generated, (e) determining changes in the position of the entry point, target point and any regions into which entry by the interventional procedure is forbidden in the second image of the plurality of images, and (f) repeating step (c) on the second image of the plurality of images based on the changes in position determined in step (e).

Any of the above described methods, may include the step of determining a cyclic motion sequence in the images, and selecting one or more of the images in the cyclic sequence in order to perform interventional steps of the procedure at the times associated with the one or more images.

Additionally, in any of the above described methods, the plurality of time-separated images may be generated over a predetermined period of time. Furthermore, in any of the above described methods, the changes in the position of the entry point, target point and any regions into which entry by the interventional procedure is forbidden may arise from cyclic motion of the region of interest of the patient, such as the breathing motion of the patient. Also, the one or more regions into which entry by the interventional procedure is forbidden may include at least one of a bone, a blood vessel, a nerve, an internal organ or an implanted medical element.

Still other example implementations involve a system for planning an image-guided interventional procedure in a region of interest of a subject, comprising:

(i) a user interface adapted to receive user inputs regarding at least positions of an entry point, a target point and one or more regions into which entry by the interventional procedure is forbidden, defined on a first image of a plurality of time-separated images of the region of interest, and (ii) at least one processor adapted to:

(a) determine changes in the position of the entry point, target point and any regions into which entry by the interventional procedure is forbidden, in a second image of the plurality of images generated at a time different from that at which the first image of the plurality of images was generated, and (b) calculate at least one trajectory for the interventional procedure between the entry point and the target point, which avoids entry into any of the one or more forbidden regions, in at least the first image of the plurality of images.

Such a system may further comprise a display adapted to display at least the plurality of time-separated images. In addition, it may further comprise a memory component adapted to store at least the plurality of images, the entry point, the target point and the one or more regions into which entry by the interventional procedure is forbidden. The at least one processor may be further adapted to determine if one or more characteristics of the at least one trajectory exceeds a predetermined level along any part of its length. Additionally, the at least one processor may be further adapted to determine if one or more of the at least one trajectory is applicable to the plurality of images. In that case, the at least one processor may be further adapted to determine which trajectory of the one or more applicable trajectories is optimal for all of the plurality of images. Finally, any of the above described systems may further comprise a communication module adapted to obtain images from an imaging system.

Implementations of the method and system described above may include any of the features described in the present disclosure, including any of the features described above in relation to other method/system implementations.

It is to be understood that although the examples used throughout this disclosure relate to methods and systems for planning a path for insertion of a needle, the methods and systems are not meant to be limited to insertion of a needle but are understood to include insertion of any tool intended to be inserted into a subject's body for diagnostic and/or therapeutic purposes, such as a port, an introducer, a surgical tool, an ablation catheter or a fluid delivery tool.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

DETAILED DESCRIPTION

Reference is now made to FIGS. 1 to 3, which illustrate the need for the methods described in the present disclosure, and how an exemplary implementation of the disclosed method is implemented on the planning of a biopsy needle procedure performed on a lesion in a patient's lung. It can be understood, however, by one of ordinary skill in the art that the exemplary systems and methods described herein can be utilized with respect to procedures performed on various parts of the body, human or otherwise, including organs, tissue, and so forth.

Figure 1A:
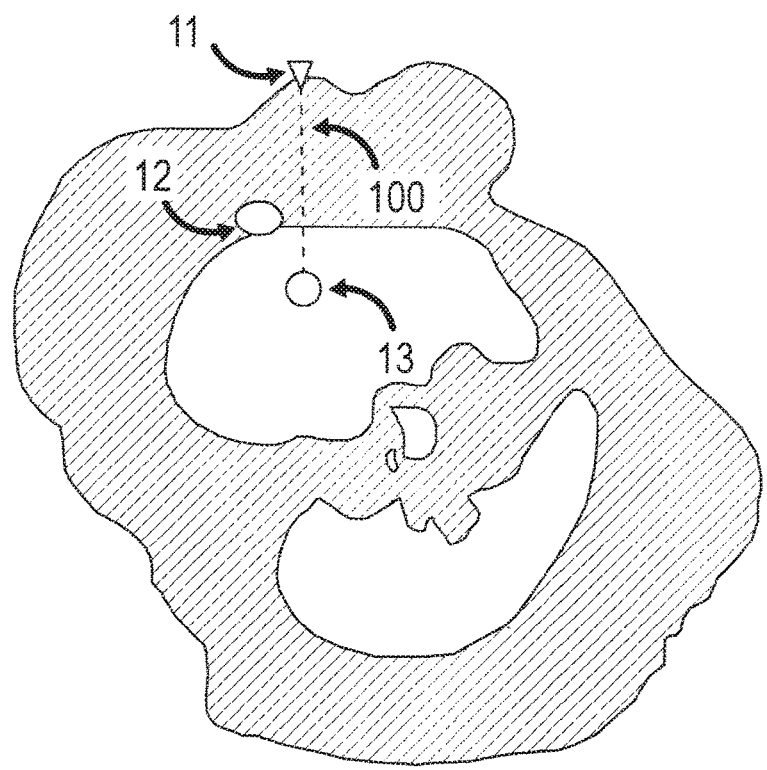
FIGS. 1A-1D are schematic illustrations of sample CT scans taken at successive points of the patient's breathing cycle, demonstrating movement of a needle entry point, target point and obstacle en route, according to some exemplary implementations of the methods of this disclosure.
Figure 1B:
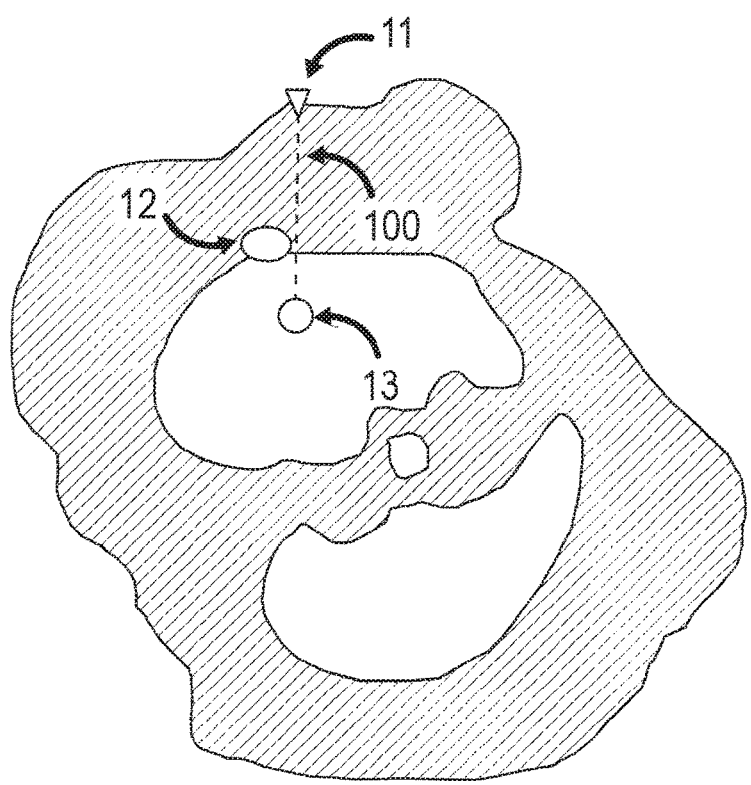
Figure 1C:
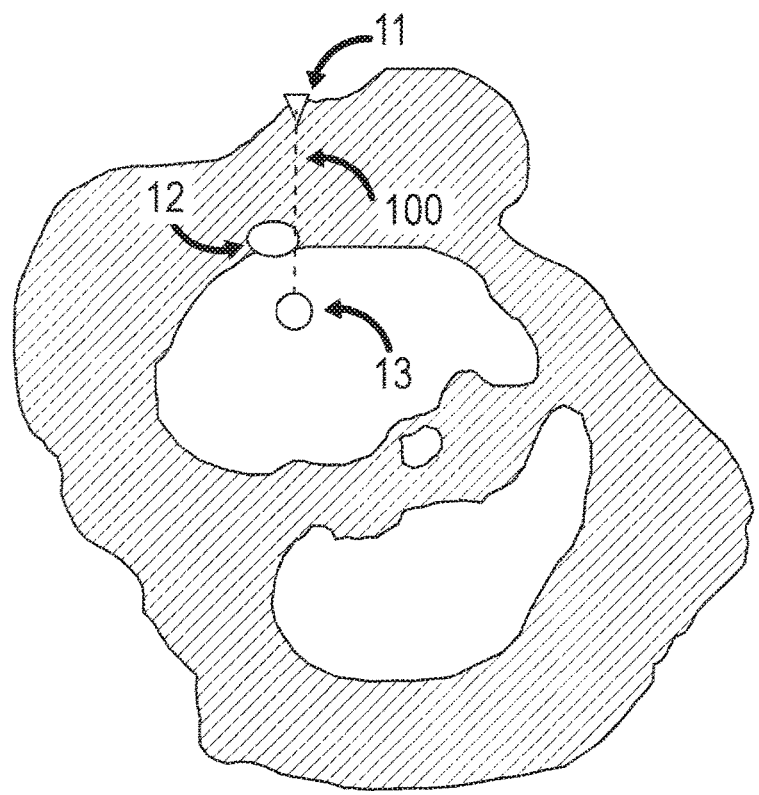
Figure 1D:
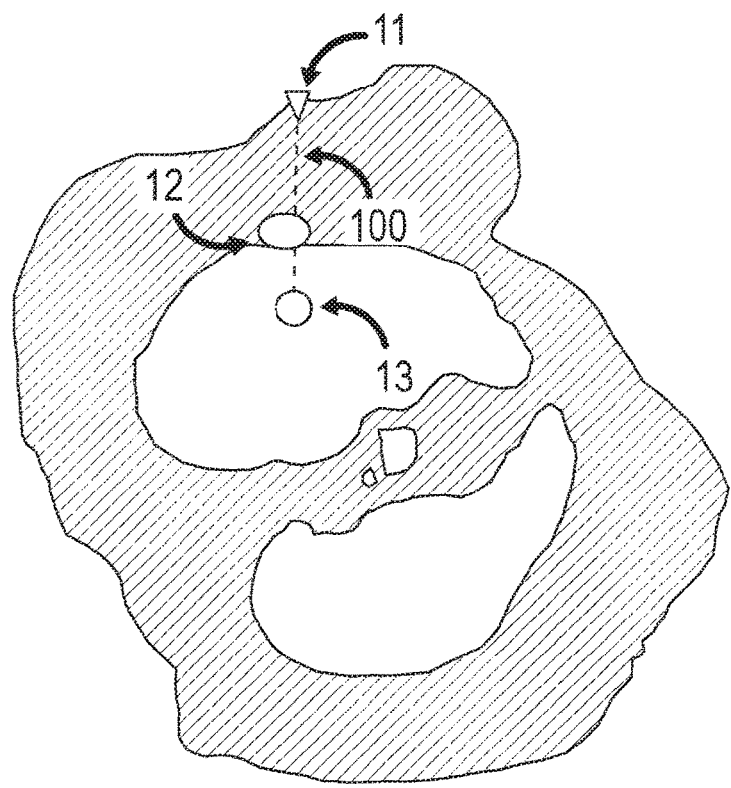

FIGS. 1A to 1D show schematic illustrations of sample CT scans of a patient's lung showing a needle entry point 11, an obstacle (in this example, the patient's rib) 12, which must be avoided by the needle trajectory and the target point 13 to be reached by the needle in the procedure. An obstacle may also be referred to throughout the present disclosure as a "forbidden area/region". Further, although a single obstacle is shown in FIGS. 1A to 1D, it can be appreciated that there can be more than one obstacle or sensitive organ/area which must be avoided during the procedure. Each of FIGS. 1A to 1D are illustrations of CT images taken at successive points of the patient's breathing cycle, such that all three reference points, i.e., the entry point 11, obstacle 12 and target point 13, move from one frame to the next. These CT images illustrate the problem of planning an insertion trajectory which will be safe and accurate despite the cyclic motion of the patient's chest due to the breathing cycle. In this example, the doctor may use the CT image shown in FIG. 1A in order to mark the obstacle 12 and the target 13 and choose an entry point 11, which enables a substantially linear trajectory 100 from the entry point 11 to the target 13, while avoiding the obstacle 12. Generally, a trajectory with minimal curvature is preferred. In FIG. 1B the relative movements of the reference points result in the planned trajectory passing very close to the obstacle 12. In FIG. 1C contact is made between the trajectory and the obstacle 12, and in FIG. 1D the planned trajectory passes straight through the obstacle 12. Thus, if the doctor were to begin the needle insertion procedure at the point of the breathing cycle corresponding to the image shown in FIG.

1D, for example, and follow his preplanned trajectory, which was based on the location of the elements in the image shown in FIG. 1A, the needle would encounter the obstacle 12 (in this example, the patient's rib) en route. This might cause needless pain to the patient, as well as result in a need to withdraw the needle and restart the insertion procedure or even the trajectory planning process.

Figure 2A:
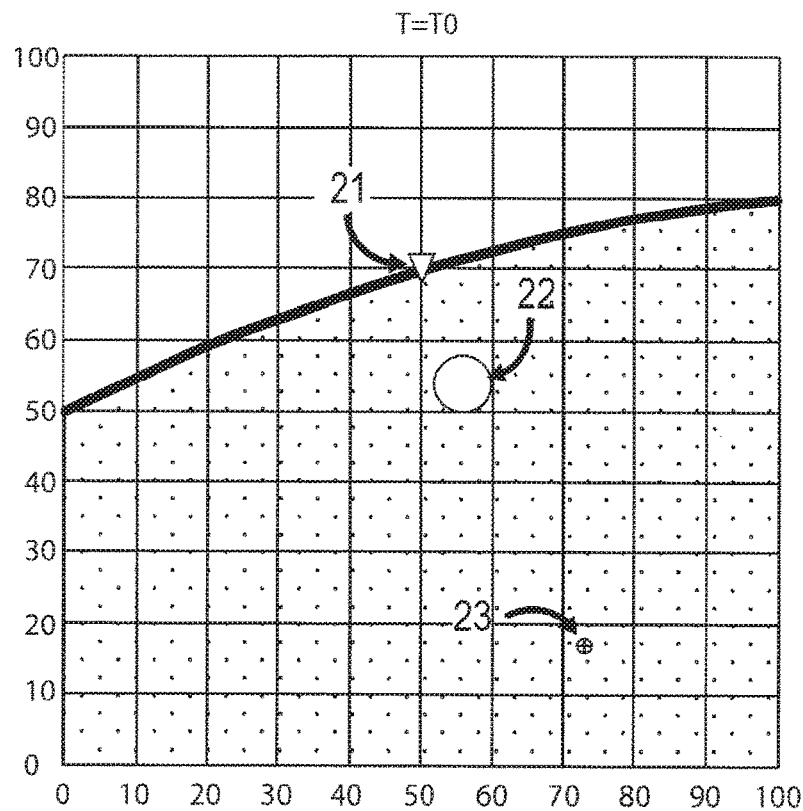
FIGS. 2A-2B are computer simulations of CT images taken at T=T0 showing a needle entry point, target point and obstacle (FIG. 2A) and a calculated trajectory (FIG. 2B), according to some exemplary implementations of the methods of this disclosure.
Figure 2B:
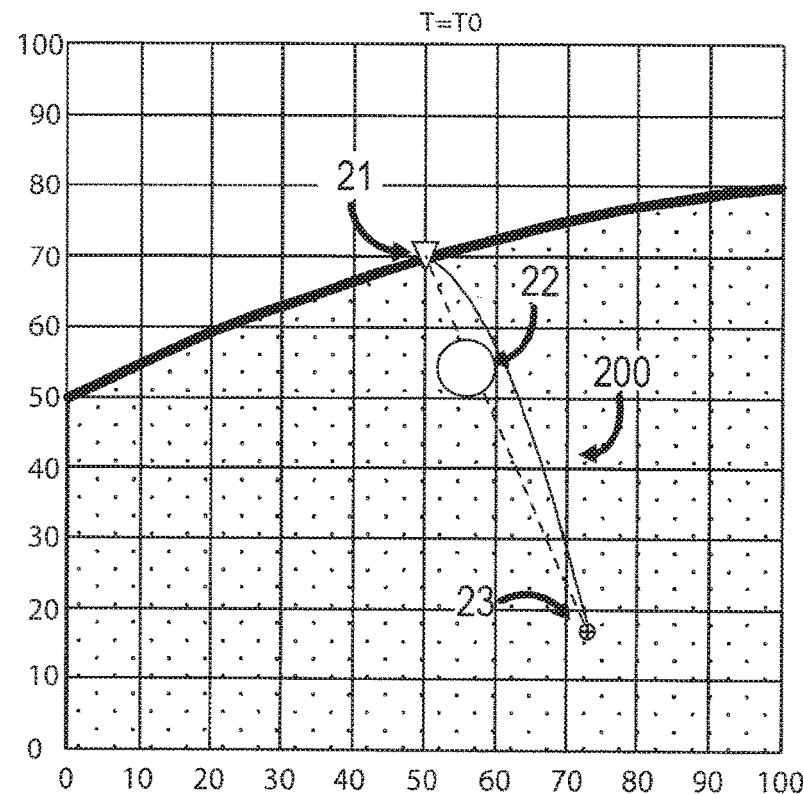

FIGS. 2A and 2B are computer simulations of a situation similar to that of the schematic illustrations of the CT images shown in FIGS. 1A to 1D. FIG. 2A shows the needle entry point 21, an obstacle 22 which must be avoided by the needle trajectory, and the target point 23 to be reached by the needle, as marked by the doctor on the computer simulation of the CT frame at the initial time of the planning method, defined as the first frame at T=T0. FIG. 2B shows a software calculated trajectory for the needle to provide the optimal path 200 between the entry point 21 and the target point 23, while avoiding the obstacle 22. In some implementations the optimal path is the path resulting in minimal needle curvature, since this imparts minimal lateral pressure on the tissue. See, for example, U.S. Pat. No. 8,348,861 to Glozman et al, for "Controlled Steering of a Flexible Needle", incorporated herein by reference in its entirety. It is noted that although the entry point is marked by a triangle, the orientation of the triangle does not reflect the entry angle. Further, it can be appreciated that the marked obstacle may reflect the exact shape and size of the obstacle itself or it may include a safety region around the obstacle.

FIGS. 3A to 3H are exemplary computer simulations similar to that of FIG. 2B, of frames taken at T=T1 to T8, subsequent to that taken at T=T0, showing how the software, having detected movement of the obstacle 22 and the target point 23, relative to the entry point 21 and to each other, by image processing of the actual CT images of each of these frames, recalculates the optimal trajectory 200 for each positional situation. In some implementations, the recalculation of the trajectory for each of the images may be based on the initial trajectory calculated at T=T0. For example, the software may first check if the initial calculated trajectory remains optimal given the new positional situation, or at least safe and acceptable, for the current image, and if not—insert as minimal adjustments as possible to the initial calculated trajectory. In other implementations, the recalculation of the optimal trajectory may be based on the trajectory calculated for the previous image (chronologically). In further implementations, the optimal trajectory may be recalculated for each image separately, with no dependency on previous or other images, i.e., as a stand-alone image. As noted in this exemplary series of frames, between the frames at times T3 and T4, shown in FIGS. 3C and 3D, the software may have determined, according to some implementations in which the trajectory recalculation is based on an initial planned trajectory, that the obstacle 22 has moved too far into the original trajectory planned on the right-hand side of the obstacle 22 (right hand as determined in the drawings of this disclosure), such that the minimal achievable curvature exceeds a predetermined maximal threshold, and has amended the initial entry angle at T0 in order to attempt to provide a more optimally selected trajectory generated on the left-hand side of the obstacle, Excessive curvature may generate excessive lateral pressure on the tissue of the patient and thus might cause discomfort or even harm to the patient. Further, excessive curvature might cause the needle to deform or even break during the procedure. It can be appreciated that the predetermined maximal curvature may depend on the type of needle intended to be used in the procedure, as the degree of achievable curvature correlates to the thickness and diameter (gauge) of the needle. In other implementations, in which the optimal trajectory is recalculated for each image as a stand-alone image, the system software may have determined, between the frames at times T3 and T4, shown in FIGS. 3C and 3D, that a trajectory generated on the left-hand side of the obstacle is preferable for the image taken at T=T4, FIG. 3D, since it allows for a smaller curvature than in any trajectory generated on the right-hand side of the obstacle, even if the curvature achievable on the right-hand side of the obstacle does not exceed the predetermined threshold. As is apparent from the subsequent frames from T4 to T8, FIGS. 3D to 3H, this alternative entry angle enabled the generation of a trajectory having lesser curvature through the remaining sequence, than would have been obtained had the originally planned trajectory to the right of the obstacle been continued.

Figure 3A:
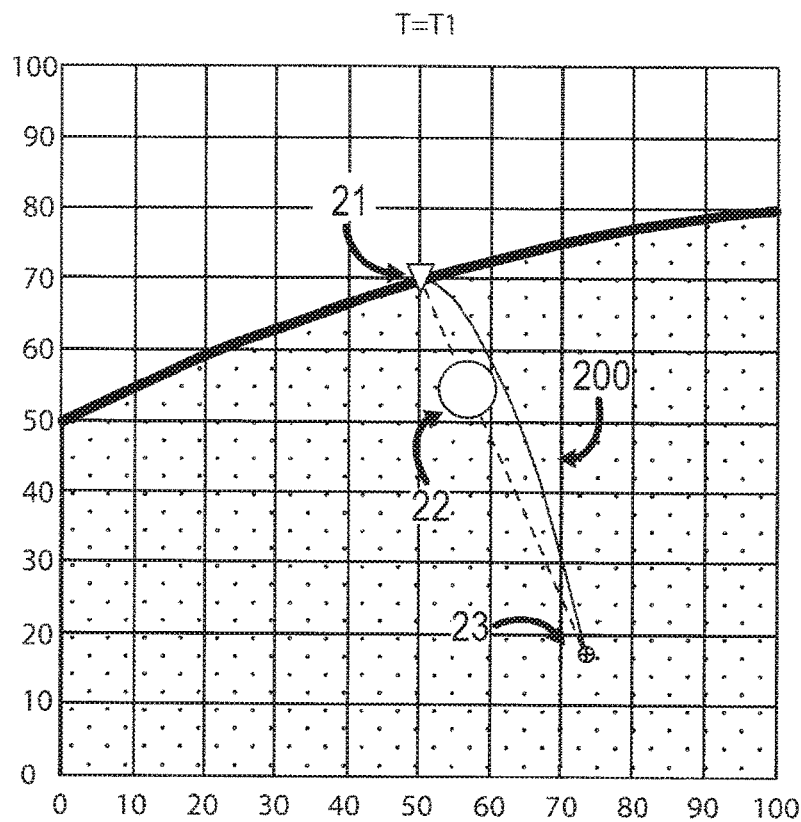
FIGS. 3A-3I are computer simulations of CT images taken at T=T1 to T8 demonstrating recalculations of the optimal trajectory for each positional situation of the entry point, target and obstacle, according to some exemplary implementations of the methods of this disclosure.
Figure 3B:
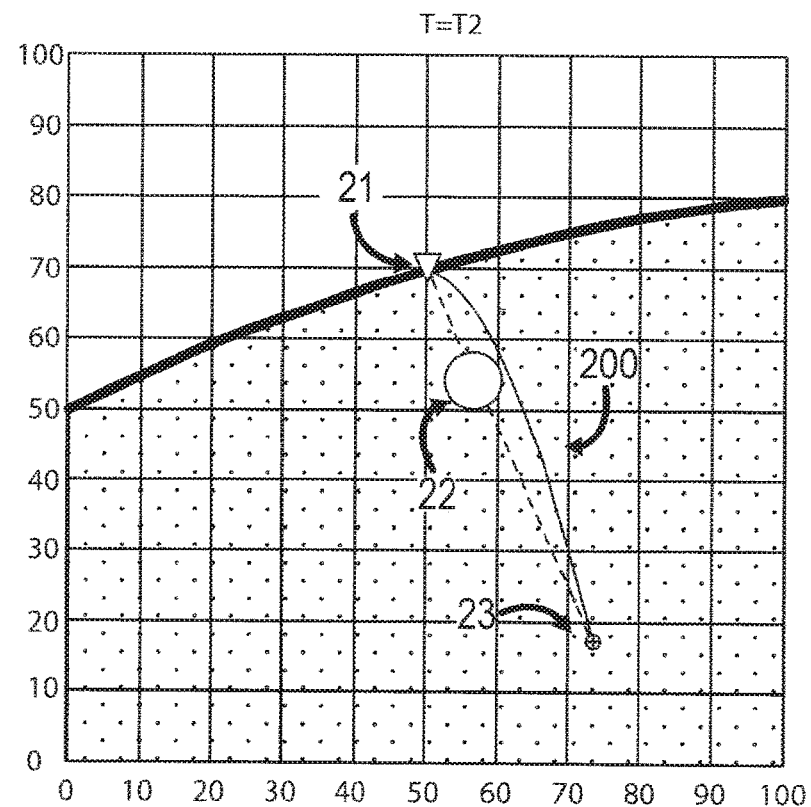
Figure 3C:
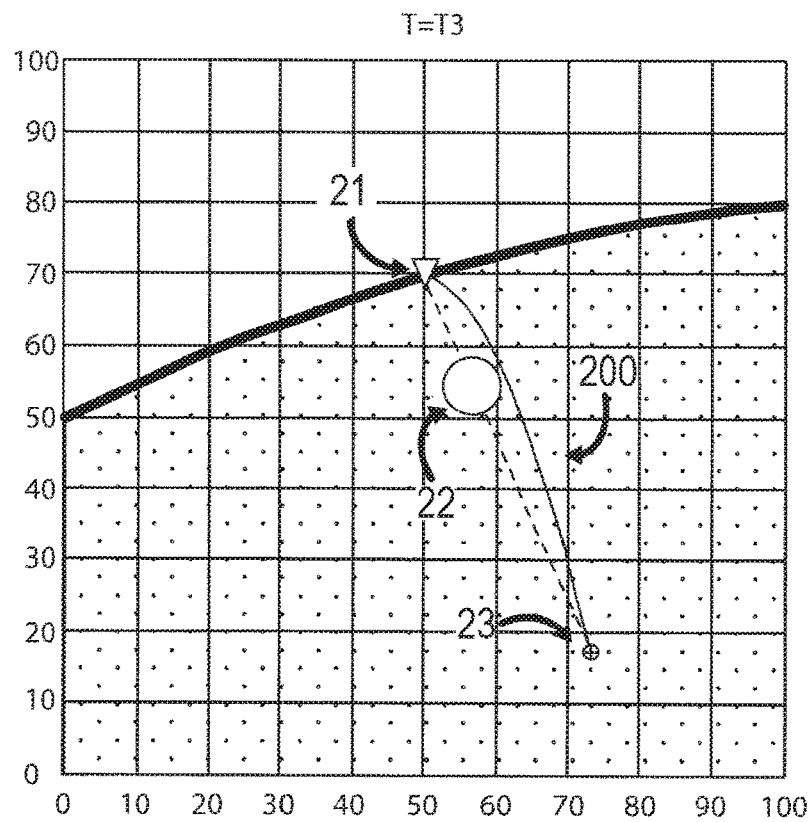
Figure 3D:
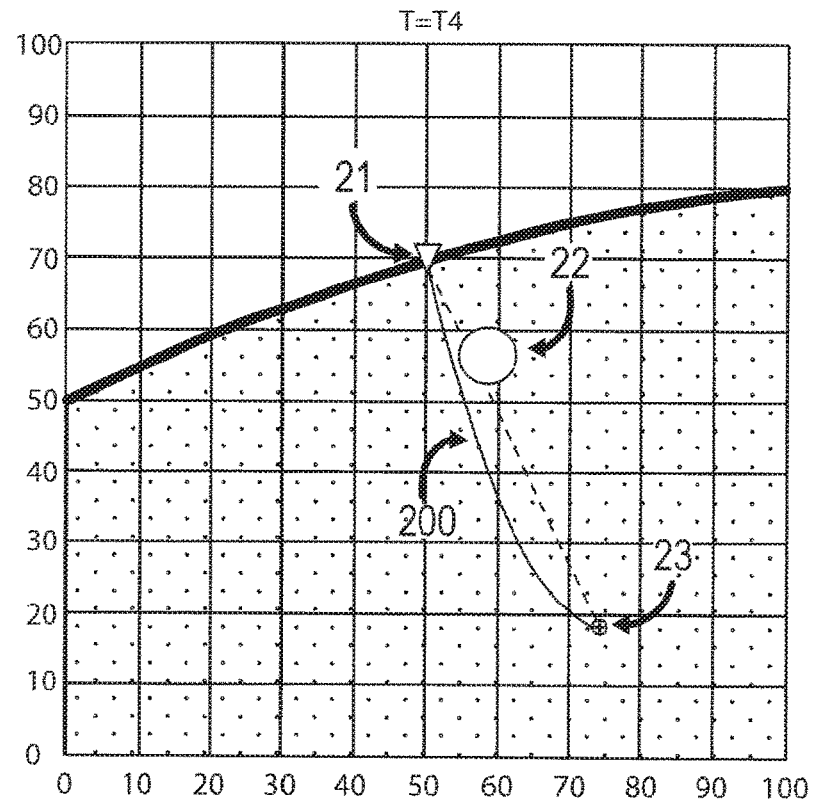
Figure 3E:
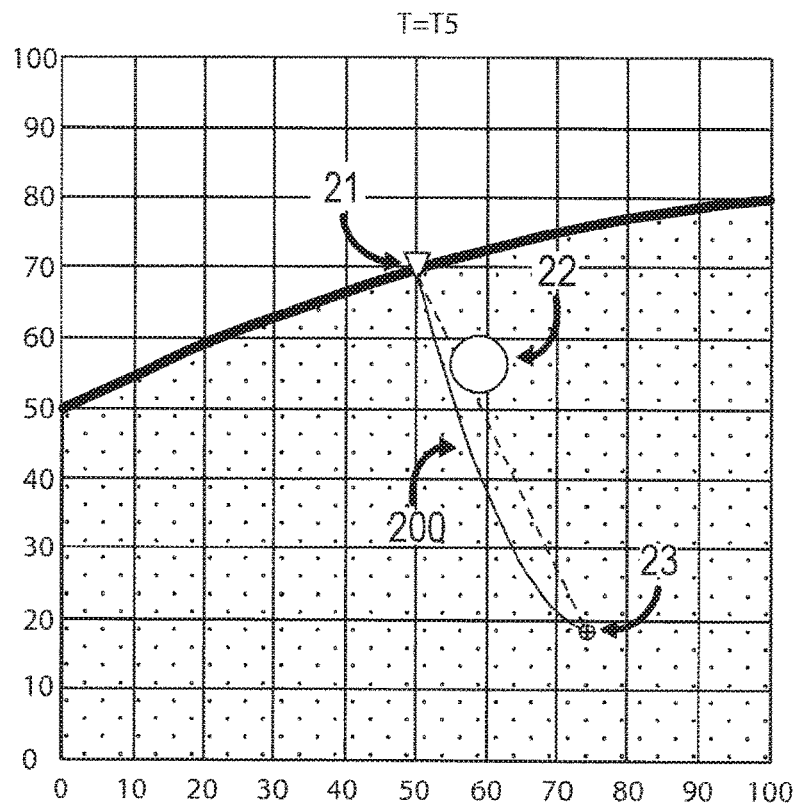
Figure 3F:
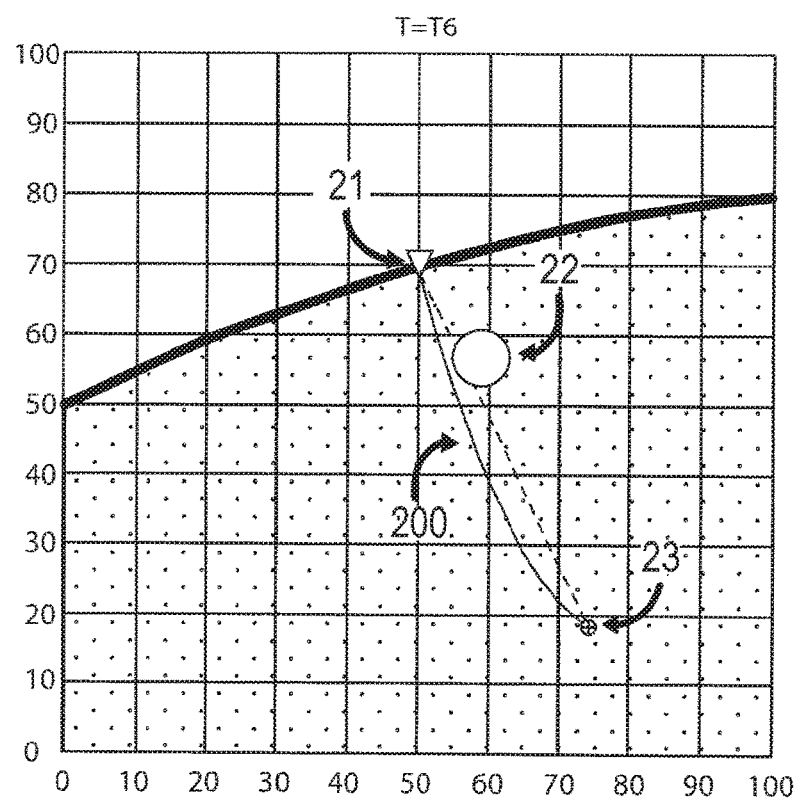
Figure 3G:
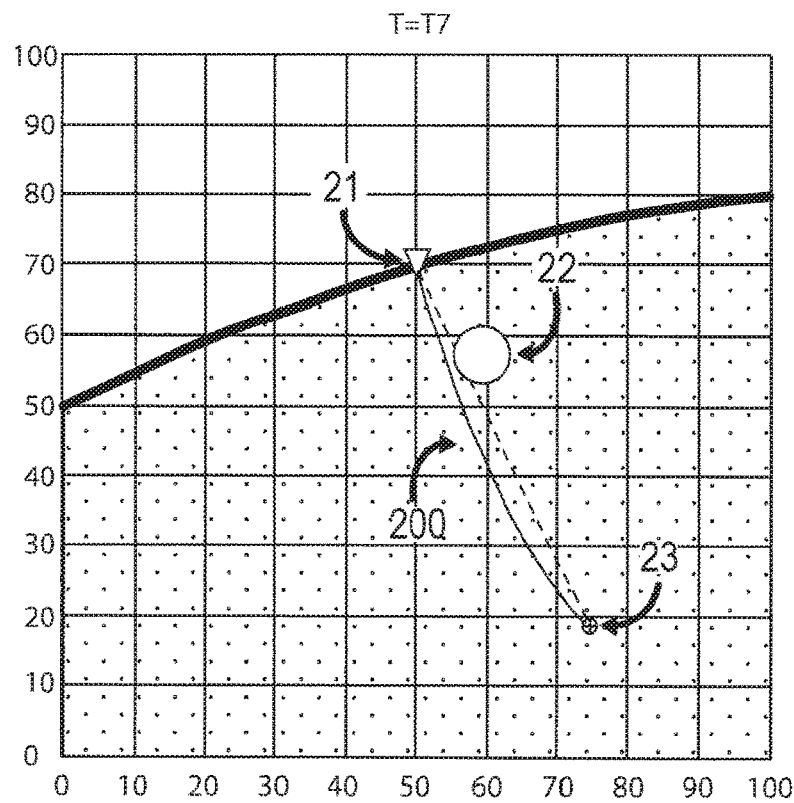
Figure 3H:
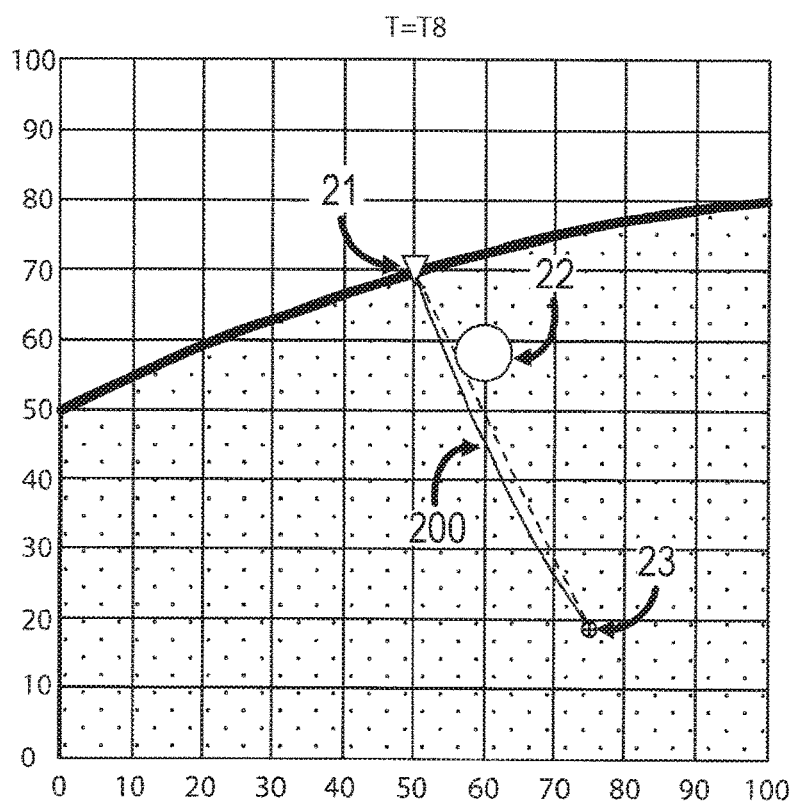
Figure 3I:
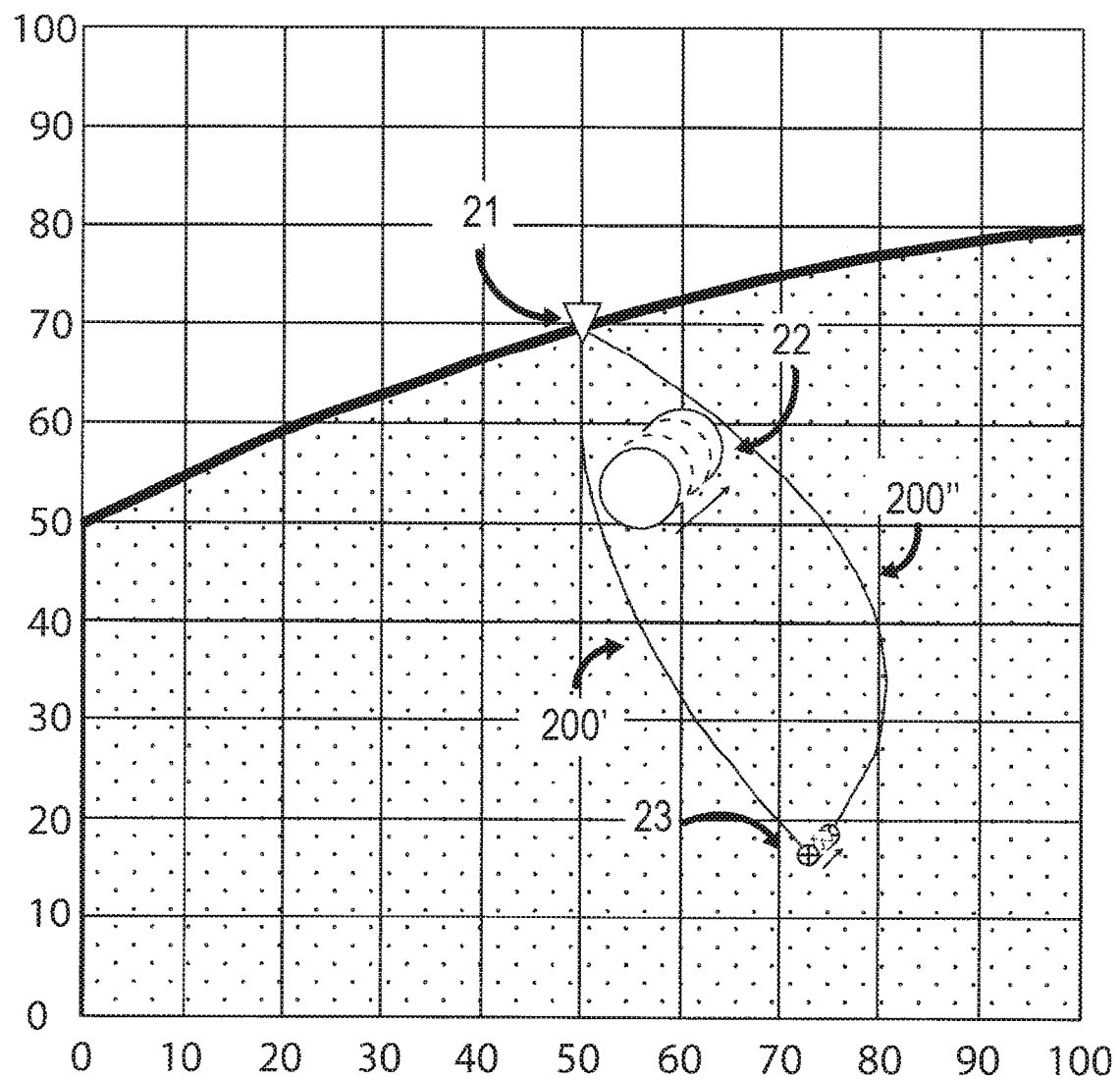

FIG. 3I is a computer simulation demonstrating the movement of the obstacle 22 and the target point 23 throughout the entire exemplary sequence shown in FIGS. 3A to 3H, i.e., in all the images taken from T=T0 to T=T8. Also shown are the trajectory 200' with the maximal curvature on the left-hand side of the obstacle, which would have been reached at T=T0 had the initial trajectory been generated on the left-hand side of the obstacle, and the trajectory 200' with the maximal curvature on the right-hand side of the obstacle, which would have been reached at T=T8 had the originally planned trajectory to the right-hand side of the obstacle been continued. It is evident that in this example, the maximal curvature reached on the right-hand side of the obstacle is higher than the maximal curvature reached on the left-hand side of the obstacle. This is due to the initial locations of the entry point 21, the obstacle 22 and the target point 23, and the fact that the direction of movement of the obstacle 22 and the target 23 during the motion cycle in this exemplary series of frames, is upward and to the right in the frame of reference of these drawings. Thus, in this case, calculating the optimal trajectory for each of the images in the series, during the preoperative planning stage, would have indicated to the user to execute the insertion procedure to the left-hand side of the obstacle, even if at T=T0, as shown in FIG. 3A, the curvature of the best trajectory to the right-hand side of the obstacle has a lesser curvature than that of the best trajectory to the left-hand side of the obstacle, as shown in FIG. 3I.

In some implementations of the methods of this disclosure, in order to ensure that the needle trajectory will not cross paths with the obstacle, and that the initially planned trajectory will be optimal for the entire cycle, independent of when during the motion cycle the procedure is performed, the user may encircle together the time varying positions of the obstacle throughout the entire cycle, and mark them as a single larger obstacle on all the images in the series.

Figure 4:
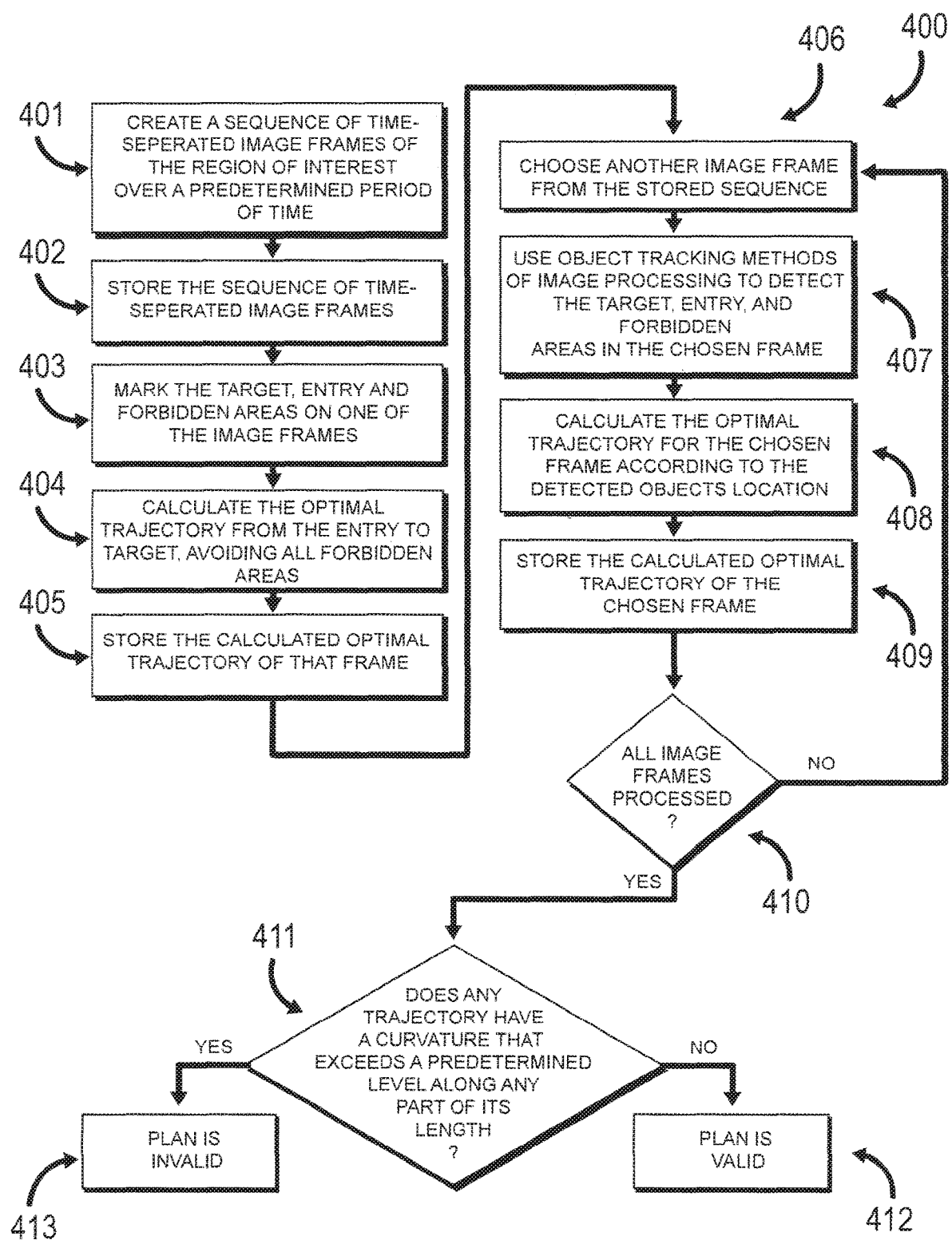
FIG. 4 is a flowchart showing one exemplary implementation of planning a needle insertion procedure.

FIG. 4 is a flowchart 400 showing the steps executed in performing one exemplary implementation of the methods described hereinabove.

In step 401, a sequence of time separated images/image frames of the region of interest is generated over a predetermined period of time. The predetermined period of time may correspond to one or more complete cycles of the patient's motion, such as the breathing cycle.

In step 402, these image frames are stored as a video sequence.

In step 403, the user selects one of the image frames, which can be anywhere in the sequence, but may conveniently be selected at a readily recognized temporal point in the motion cycle of the patient, such as at a point when the patient has completely exhaled. The user then marks on the selected image frame, the entry point which he intends using, the target point, and the region of forbidden access in the patient's anatomy. Obviously, the user selects to the best of his professional judgment, an entry point that will appear to provide the shortest trajectory to the target with the least curvature and yet still avoiding the forbidden regions. In some implementations, step 403 is performed by the system software, i.e., the program may be adapted to select the initial image frame and/or mark on the selected image frame at least one of the target point, the obstacles en route and the initial entry point.

Then, in step 404, the program calculates the optimal trajectory from the entry point to the target avoiding all forbidden areas, including determination of the entry angle of the needle at the entry point. In the case of a program option which does not calculate the entry angle, the user also has to input the entry angle which he judges to be the most appropriate entry angle for the entry point and estimated trajectory chosen. This step is not shown in the flowchart of FIG. 4, but is to be understood where appropriate.

In step 405, the optimal trajectory calculated in step 404 for the selected frame is stored.

In step 406, another image frame is selected from the stored sequence, which may most conveniently be the next frame in the sequence, but could be a frame later on in the sequence, or even a frame prior to the first selected frame, since the frame sequence is cyclical. In some implementations the user manually selects the image to be processed next. In other implementations, the system software automatically selects a new image for processing.

In step 407, the program then uses object tracking image processing methods in order to detect the newly acquired positions in the new image frame, of the entry point, the target point and the forbidden access area, these new positions having resulted from the cyclic movement of the patient.

In step 408, the program then calculates the optimal trajectory for that frame, in accordance with the new locations of the three defined reference positions—entry point, target point and forbidden access area.

In step 409, the optimal trajectory calculated for that new frame is stored.

Then, in step 410, the program ascertains whether all of the image frames of the sequence chosen have had their optimal trajectories calculated. If not, then the program returns the procedure to step 406, another image frame is chosen from the stored sequence of frames, and steps 407 to 410 are repeated for this next selected frame.

If, on the other hand, in step 410, all of the image frames of the complete sequence of frames have been processed, then the program proceeds to step 411, in which all of the calculated trajectories are examined to determine whether any of them has a curvature which exceeds the predetermined maximum defined curvature along any part of its length. It can be appreciated that curvature is only one example of a characteristic of the trajectory checked in step 411. Another characteristic may be, for example, distance from obstacles, in which case the program will check if the trajectory deviates from a minimal acceptable distance. A further characteristic may be the insertion angle, if selected automatically by the system software, as some insertion angles may be impossible to achieve due to the design of the automated insertion system (e.g., robot). A combination of several characteristics may also be checked for deviation in step 411. If no excessive trajectory curvature has been found in any of the frames, then that plan for needle insertion is regarded as a valid plan for implementing the needle insertion procedure over the whole of the patient's motion cycle, as shown in step 412. The term "valid plan" may indicate that for each of the image frames in the sequence, taken at different times during the patient's motion cycle, there is an acceptable/safe trajectory. Thus, the user may begin the needle insertion procedure at any point during the motion cycle, and the insertion procedure will be performed according to the optimal trajectory calculated for that specific point in time during the cycle. If, on the other hand, such an excessive curvature is found in any of the calculated trajectories, then that insertion plan for the needle is regarded as being invalid, as shown in step 413, and the doctor has to select an alternative entry point and/or, if relevant, an alternative entry angle. The whole procedure should then be repeated in order to attempt to obtain an insertion plan without any of the trajectories calculated for the series of image frames having an excessive curvature.

In some implementations of these methods, after optimal trajectories have been calculated separately for all of the frames in the sequence, all or at least one of the calculated trajectories may be run through all or at least several of the other frames in the sequence, and from the checked trajectories a single optimal trajectory for the entire series of frames may be selected for the needle insertion procedure. Such a trajectory may be the trajectory having the minimal curvature and/or the shortest distance from the entry point to the target point, for example.

Figure 5:
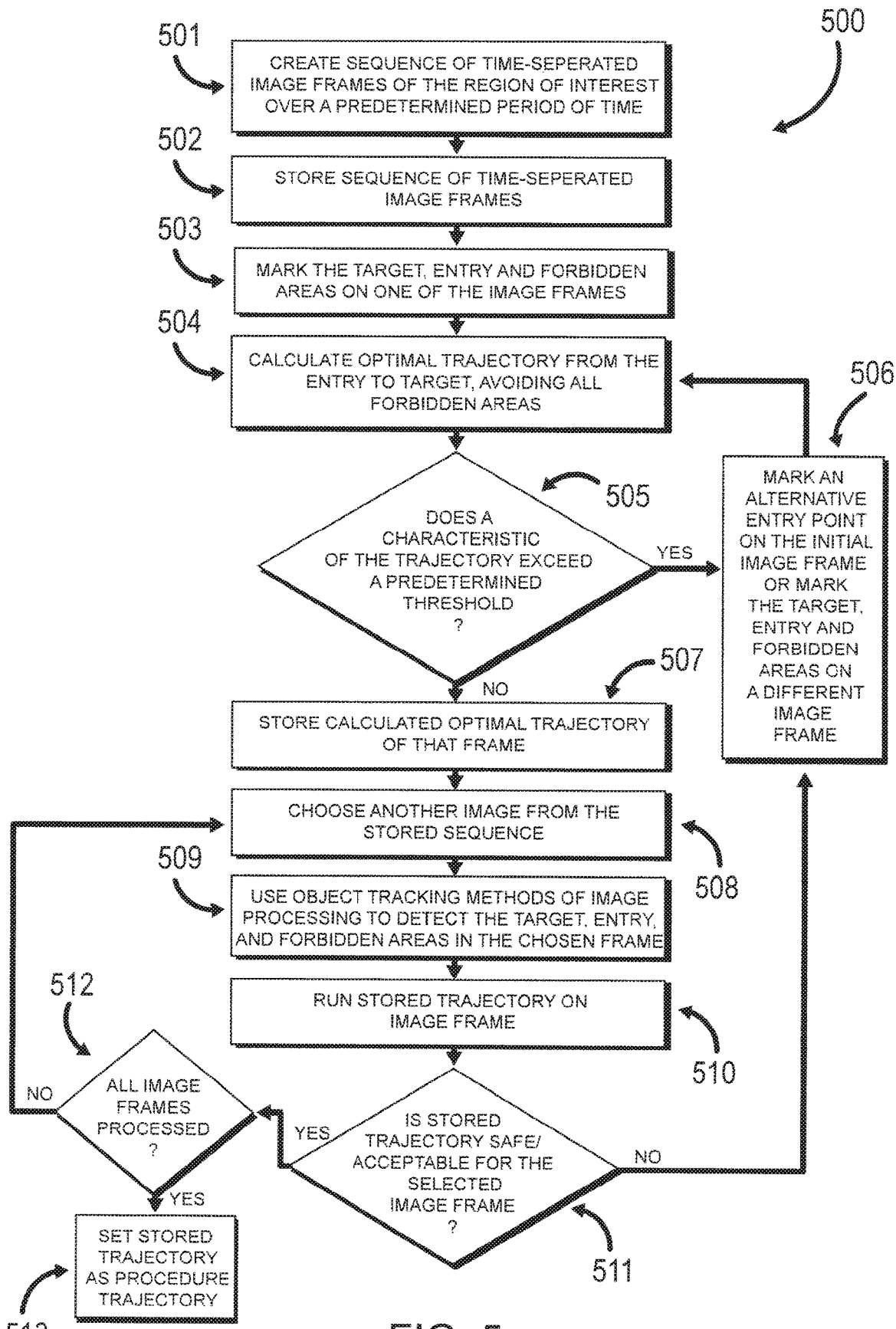
FIG. 5 is a flowchart showing another exemplary implementation of planning a needle insertion procedure.

FIG. 5 is a flowchart 500 showing the steps executed in performing another exemplary implementation of the methods of the present disclosure.

In step 501, a sequence of time separated images/image frames of the region of interest is generated over a predetermined period of time. The predetermined period of time may correspond to one or more complete cycles of the patient's motion, such as the breathing cycle.

In step 502, these image frames are stored.

In step 503, the user/doctor selects one of the image frames, and marks on the selected image frame, the entry point which he intends using, the target point, and the region of forbidden access in the patient's anatomy. In other implementations, the program may be adapted to select the initial image frame and/or to mark on the selected image frame at least one of the target point, the obstacles en route and the initial entry point.

Then, in step 504, the program calculates the optimal trajectory from the entry point to the target avoiding all forbidden areas. In some implementations, calculation of the optimal trajectory may include determination of the entry angle of the needle at the entry point. In other implementations, the user/doctor also has to input the entry angle prior to trajectory calculation.

In step 505 the program determines if a characteristic of the calculated trajectory, e.g., curvature, exceeds a predetermined threshold. If so, then in step 506 the doctor has to select an alternative entry point and/or an alternative entry angle for the initially selected frame, or choose a different image frame for which the trajectory will be calculated, and steps 504 and 505 are repeated. If no relevant characteristic exceeds a predetermined threshold, then the calculated optimal trajectory is stored, in step 507. Another characteristic may be, for example, distance from obstacles. In such a case, determining if a characteristic of the trajectory exceeds a predetermined threshold may mean that the program determines if the distance between the calculated trajectory and a marked obstacle is less than a minimal acceptable distance.

In step 508, another image frame is selected from the stored sequence, which may most conveniently be the next frame in the sequence, but could be a frame later on in the sequence, or even a frame prior to the first selected frame, since the frame sequence is cyclical. In some implementations the user/doctor manually selects the image to be processed next. In other implementations, the system software automatically selects a new image for processing.

In step 509, the program uses object tracking image processing methods in order to detect the newly acquired positions in the new image frame, of the entry point, the target point and the forbidden access area, which having resulted from the cyclic movement of the patient.

In step 510, the program runs the stored trajectory on the image frame selected in step 508, taking into account the new positions of the entry point, the target point and the forbidden area.

Then, in step 511, the program checks if the stored trajectory is acceptable/safe for the selected image frame. Acceptable/safe (or—applicable) may mean that the trajectory leads from the entry point to the target point, while avoiding the obstacle, given the newly acquired positions of these elements. In some cases, the automated insertion system used for executing the calculated trajectory may be adapted to adjust the trajectory during the insertion process, e.g., a closed-loop system, such as the systems disclosed in U.S. Pat. No. 8,348,861, to Glozman et al, for "Controlled Steering of a Flexible Needle", and U.S. Pat. No. 8,663,130 to Neubach et al, for "Ultrasound Guided Robot for Flexible Needle Steering", both incorporated herein by reference in their entireties. In such cases, the checked trajectory may be also considered acceptable/safe if in order for it to reach the target and/or avoid the obstacle, an acceptable level of adjustment will be required.

If the program determines that for that image frame the stored trajectory is not safe/acceptable, i.e., it does not reach the target point and/or it encounters the obstacle en route and/or an unacceptable level of adjustment will be required during the insertion procedure in order for it to reach the target and/or avoid the obstacle, then the process returns to step 506 and the doctor has to select an alternative entry point and/or an alternative entry angle for the initially selected frame, or choose a different image frame for which the trajectory will be calculated. If, on the other hand, the program determines that for the currently processed image frame the stored trajectory is acceptable/safe, then it proceeds to step 512, in which it ascertains if all of the image frames of the complete sequence of frames have been processed, i.e., if the stored optimal trajectory has been run through all of the image frames in the series. If not, then the program returns the procedure to step 508, and another image frame is chosen from the stored sequence of frames, and steps 509 to 512 are repeated for this next selected frame. If, on the other hand, in step 512, all of the image frames of the complete sequence of frames have been processed, meaning that the stored optimal trajectory has been run through all of the image frames in the series, and it has been determined that for each of the images the stored trajectory is acceptable/safe, then the stored trajectory is set, in step 513, as the trajectory for the insertion procedure.

Figure 6:
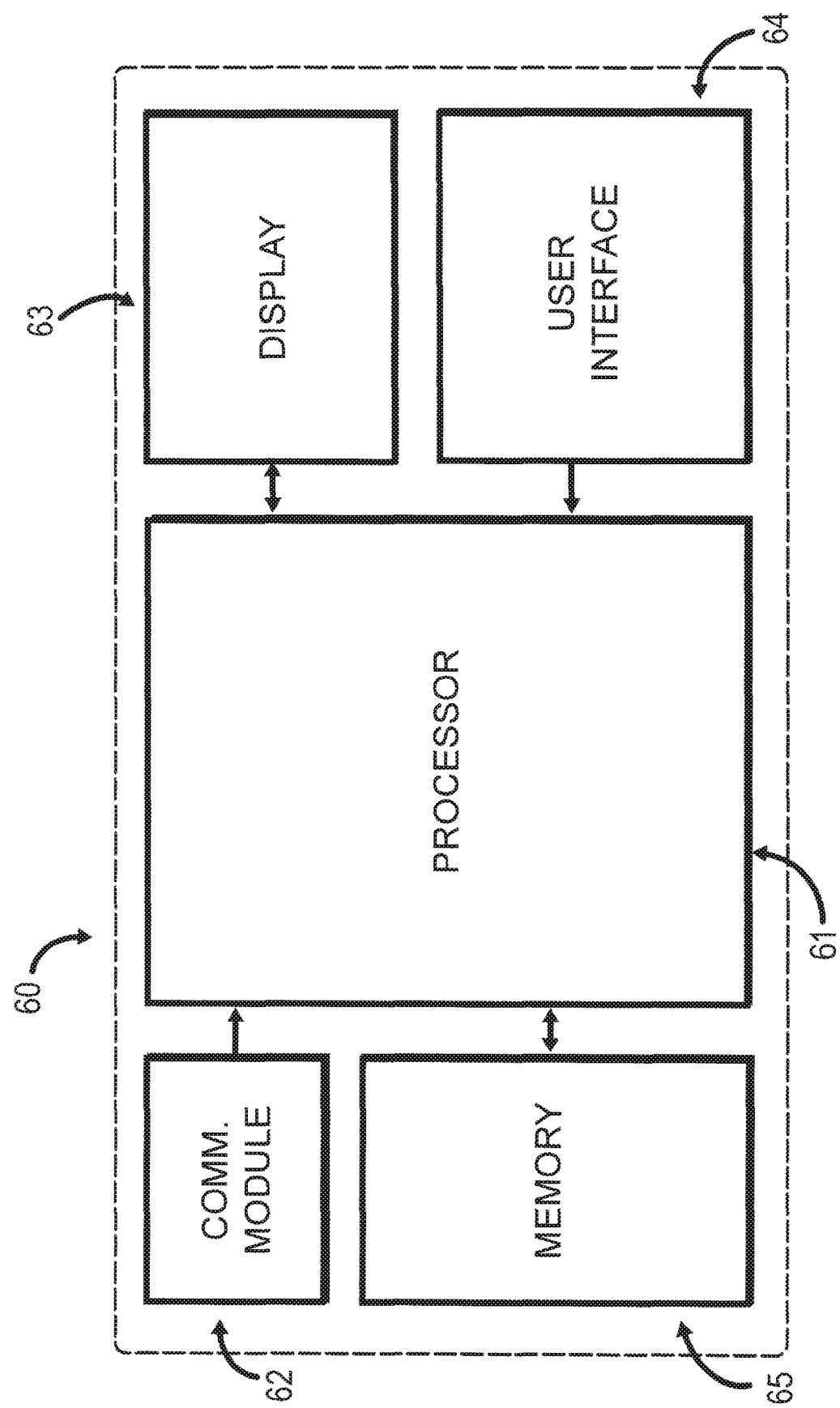
FIG. 6 is a block diagram of an exemplary system for planning a needle insertion procedure.

FIG. 6 is a block diagram of an exemplary system 60 for executing any of the above described methods, though it is to be understood that other system configurations may also be envisaged. The system may include at least one processor 61 for determining changes in the positions of the entry point, target point and any obstacles therebetween, using object tracking methods of image processing. The at least one processor 61 may be further adapted to calculate needle trajectories, and in some implementations, to analyze the calculated trajectories and compare them to one another. The processor 61 may be incorporated in a personal computer (PC), a laptop, a tablet, a smartphone or any other processor-based device. In some implementations, the system may include a communication module 62 for communicating with and/or retrieving images from an imaging system (e.g., a CT system, an MRI system, an ultrasonic system or an X-ray fluoroscopic system). The communication module 62 may be integrated with the processor or it may be a separate component. In some implementations, the images of the patient's region of interest may be uploaded or read directly from an external memory device, such as a CD, DVD, USB portable drive, etc. The system may further include a display/screen 63 for displaying, inter alia, the obtained images and the calculated trajectories. The system may also include a user interface 64 to enable the user/doctor to mark the entry point, target and forbidden areas on the images obtained from the imaging system. In some implementations, the user interface 64 may also be used for verification and acceptance of the calculated trajectory by the user. The user interface 64 may be in the form of buttons, switches, keys, a keyboard, a computer mouse, a joystick, a touch-sensitive screen, etc. The display 63 and user interface 64 may be two separate components, or they may form together a single component, in case a touch-sensitive screen ("touch screen"), for example, is utilized. The system may further include a memory component 65 for storing the obtained images, the marked entry point, target point and obstacle/s, the calculated trajectories, etc., and the at least one processor 61 may be further adapted to store the above data in the memory component 65 as well as retrieve it therefrom.

Although a few variations have been described in detail above, other modifications are possible. For example, the logic flows depicted in the accompanying figures and described herein do not require the particular order shown, or sequential order, to achieve desirable results.

Although particular implementations have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the disclosure as defined by the claims. Other aspects, advantages, and modifications are considered to be within the scope of the following claims. The claims presented are representative of the implementations and features disclosed herein. Other unclaimed implementations and features are also contemplated. Accordingly, other implementations are within the scope of the following claims.

The invention claimed is:

1. A method of pre-operatively planning an image-guided insertion procedure for inserting a tool into a tissue in a region of interest of a subject, comprising:
   (a) obtaining a plurality of time-separated images of the region of interest, said plurality of time-separated images derived at different times during the breathing cycle of said subject;
   (b) defining on a first image of said plurality of time-separated images an entry point for entry of said tool into said tissue, a target point and one or more forbidden regions into which entry by said tool during said insertion procedure is forbidden;
   (c) calculating on said first image a first trajectory for said insertion procedure between said entry point and said target point; which avoids entry into all of said one or more forbidden regions;

(d) determining the positions of said entry point, said target point and said one or more forbidden regions in one or more other images of said plurality of time-separated images;

(e) calculating; on at least one of said one or more other images; at least one new trajectory between said entry point and said target point; which avoids entry into all of said one or more forbidden regions, based on the positions of said entry point, said target point and said one or more forbidden regions in said at least one of said one or more other images, as determined in step (d);

(f) checking for each of said first trajectory and at least one new trajectory, one or more trajectory characteristics selected from: (i) the curvature, (ii) the entry angle at said entry point, and (iii) the proximity to any of said one or more forbidden regions, to determine if one or more predetermined levels relating to said one or more trajectory characteristics is exceeded; and (g) if said one or more predetermined levels relating to said one or more trajectory characteristics are determined not to be exceeded in each of said first trajectory and at least one new trajectory, ascertaining pre-operatively that said first trajectory and said at least one new trajectory are suitable trajectories for said insertion procedure.

2. A method according to claim 1, wherein if at least one of said one or more predetermined levels relating to said one or more trajectory characteristics is determined to be exceeded, the method further comprises the steps of:
defining an alternative entry point on said first image; and repeating steps (c) to (g) using said alternative entry point with said target point and said one or more forbidden regions initially defined in step (b).

3. A method according to claim 1, wherein determining the positions of said entry point, said target point and said one or more forbidden regions in said one or more other images in step (d) is performed using one or more object tracking image processing methods.

4. A method according to claim 1, wherein the one or more forbidden region includes at least one of: a bone, a blood vessel; a nerve, an internal organ and an implanted medical element.

5. A method according to claim 1, wherein said tool is any one of: a needle, a port, an introducer, an ablation catheter, a surgical tool or a fluid delivery tool.

6. A system for pre-operatively planning an image-guided insertion procedure for inserting a tool into a tissue in a region of interest of a subject; comprising:
a user interface configured to receive user inputs regarding at least positions of an entry point for entry of said tool into said tissue, a target point and one or more forbidden regions into which entry by said tool during said insertion procedure is forbidden, defined on a first image of a plurality of time-separated images of the region of interest derived at different times during the breathing cycle of said subject; and
at least one processor configured to:
determine the positions of said entry point, said target point and said one or more forbidden regions in at least one other image of said plurality of time-separated images;
calculate at least one trajectory for said needle insertion procedure between said entry point and said target point, which avoids entry into all of said one or more forbidden regions, in at least said first image of said plurality of time-separated images;
check for said calculated at least one trajectory, one or more trajectory characteristics selected from: (i) the curvature, (ii) the entry angle at said entry, point, and (iii) the proximity to each of said one or more forbidden regions, to determine if at least one pre-determined level relating to said one or more trajectory characteristics is exceeded; and
if said one or more predetermined levels relating to said one or more trajectory characteristics are determined not to be exceeded, ascertain pre-operatively that said calculated at least one trajectory is a suitable trajectory for said insertion procedure.

7. A system according to claim 6, further comprising a display configured to display at least said plurality of time-separated images.

8. A system according to claim 6, further comprising a memory component configured to store at least said plurality of time-separated images, said entry point, said target point and said one or more forbidden regions.

9. A system according to claim 6, further comprising a communication module configured to obtain said plurality of time-separated images from an imaging system.

10. A system according to claim 6, wherein said tool is any one of: a needle, a port, an introducer, an ablation catheter, a surgical tool, or a fluid delivery tool.

11. A method of pre-operatively planning an image-guided insertion procedure for inserting a tool into a tissue in a region of interest of a subject, comprising:

(a) obtaining a plurality of time-separated images of the region of interest;

(b) defining on a first image of said plurality of time-separated images an entry point for entry of said tool into said tissue, a target point and one or more forbidden regions into which entry by said tool during said insertion procedure is forbidden;

(c) calculating on said first image a first trajectory for said insertion procedure between said entry point and said target point, which avoids entry into all of said one or more forbidden regions;

(d) determining the positions of said entry point, said target point and said one or more forbidden regions in one or more other images of said plurality of time-separated images;

(e) calculating, on at least one of said one or more other images, at least one new trajectory between said entry point and said target point, which avoids entry into all of said one or more forbidden regions, based on the positions of said entry point, said target point and said one or more forbidden regions in said at least one of said one or more other images, as determined in step (d);

(f) calculating, for each of said first trajectory and said at least one new trajectory, the maximal curvature level;

(g) comparing the calculated maximal curvature level to a predetermined maximal curvature level; and (h) if the calculated maximal curvature level of each of said first trajectory and said at least one new trajectory is determined not to exceed said predetermined maximal curvature level, ascertaining pre-operatively that said first trajectory and said at least one new trajectory are suitable trajectories for said insertion procedure.

12. A method according to claim 11, wherein if the calculated maximal curvature level of at least one of said first trajectory and said at least one new trajectory exceeds said predetermined maximal curvature level, the method further comprises the steps of:
defining an alternative entry point on said first image; and repeating steps (c) to (h) using said alternative entry point with said target point and said one or more forbidden regions initially defined in step (b).

\* \* \* \* \*